United States Patent [19]
Hansenne

[11] Patent Number: 5,635,163
[45] Date of Patent: Jun. 3, 1997

[54] SCREENING COSMETIC COMPOSITIONS CONTAINING A HYDROPHILIC AGENT COMPRISING AT LEAST ONE SULPHONIC ACID RADICAL

[75] Inventor: Isabelle Hansenne, Paris, France

[73] Assignee: L'Oreal, Paris, France

[21] Appl. No.: 387,781

[22] PCT Filed: Jun. 21, 1994

[86] PCT No.: PCT/FR94/00751

§ 371 Date: Apr. 7, 1995

§ 102(e) Date: Apr. 7, 1995

[87] PCT Pub. No.: WO95/00111

PCT Pub. Date: Jan. 5, 1995

[30] Foreign Application Priority Data

Jun. 21, 1993 [FR] France ................................ 93 07447

[51] Int. Cl.$^6$ ........................... A61K 7/44; A61K 7/42
[52] U.S. Cl. ................... 424/60; 424/47; 424/59
[58] Field of Search .................... 424/47, 59, 60, 424/61

[56] References Cited

U.S. PATENT DOCUMENTS

| | | | |
|---|---|---|---|
| 3,670,074 | 6/1972 | Doner | 424/60 |
| 4,585,597 | 4/1986 | Lang et al. | 514/510 |
| 4,710,584 | 12/1987 | Lang et al. | 560/51 |
| 4,775,526 | 10/1988 | Lang et al. | 424/47 |
| 5,004,594 | 4/1991 | Richard et al. | 424/47 |

FOREIGN PATENT DOCUMENTS

| | | |
|---|---|---|
| 0275719 | 7/1988 | European Pat. Off. . |
| 0390682 | 10/1990 | European Pat. Off. . |
| 0445700 | 9/1991 | European Pat. Off. . |
| 0518772 | 12/1992 | European Pat. Off. . |
| 472220 | 4/1966 | Germany . |
| 2407733 | 2/1974 | Germany . |
| 2025957 | 8/1980 | United Kingdom . |
| 2121801 | 1/1984 | United Kingdom . |
| 2185019 | 7/1987 | United Kingdom . |

OTHER PUBLICATIONS

Patent Abstracts of Japan, vol. 17, No. 185, (C–1047) 12 Apr. 1993 and JP-A-04 338 317 (KAO CORP) 25 Nov. 1992.

Database WPI, Week 9311, Derwent Publications Ltd., London, GB; AN 93–088577 and JP-A-5 032 532 (SHISEIDO CO LTD) 9 Feb. 1993.

*Primary Examiner*—Shelley A. Dodson
*Attorney, Agent, or Firm*—Burns, Doane, Swecker & Mathis, L.L.P.

[57] ABSTRACT

The invention relates to screening cosmetic compositions containing at least one hydrophilic agent which screens ultraviolet radiation and contains at least one sulphonic acid radical —$SO_3H$ and at least one amino-functional silicone derivative.

Application to the protection of skin and hair against the effects of ultraviolet radiation.

53 Claims, No Drawings

SCREENING COSMETIC COMPOSITIONS CONTAINING A HYDROPHILIC AGENT COMPRISING AT LEAST ONE SULPHONIC ACID RADICAL

This application is a Rule 371 continuation of PCT/FR94/00751, filed on Jun. 21, 1994.

The present invention relates to substantive and water-resistant cosmetic compositions which are intended to protect the skin and hair from ultraviolet radiation. It relates more particularly to substantive and water-resistant cosmetic compositions containing a hydrophilic UV screening agent comprising at least one sulphonic acid radical. The invention also relates to their use for the protection of skin and hair against ultraviolet radiation.

It is well known that luminous radiation with wavelengths of between 280 nm and 400 nm allow the human skin to tan, and that rays with wavelengths of between 280 and 320 nm, known by the term UV-B, cause erythemas and skin burns which may damage the development of the tan; this UV-B radiation must therefore be screened.

It is also known that UV-A rays, with wavelengths of between 320 and 400 nm, which cause the skin to tan, are capable of harming the latter, especially in the case of a sensitive skin or a skin which is continually exposed to solar radiation. In particular, UV-A rays cause a loss of skin elasticity and the appearance of wrinkles leading to premature ageing. They promote the triggering of the erythemal reaction or accentuate this reaction in certain subjects and can even be the cause of phototoxic or photoallergic reactions. It is therefore desirable to screen the UV-A radiation as well.

In the context of the present invention, substantivity may be characterized by the hydrophobic nature of the screening combination, that is to say its non-dissociation in waters water resistance may be defined by the stability over time, after showering or bathing, of the protection index in UVA and/or UVB.

Proposals have already been made to improve the substantivity and water-resistance of screening compositions by formulating them either with polymers (see in particular patent U.S. Pat. No. 5,041,281 and patent application JP-A-05 032 532), or in a vehicle comprising a water-in-oil emulsion in the presence of emulsifiers having a HLB (hydrophilic-lipophilic balance) varying from 1 to 7 (see in particular patent U.S. Pat. No. 5,047,232).

These two techniques make it possible effectively to enhance the water resistance of the compositions when they contain lipophilic sunscreen agents. However, it is not the case with the compositions containing hydrophilic sunscreen agents, especially acids, since the latter disappear in water, when bathing in the sea or in a swiping pool, under the shower or when engaging in water sports; thus the anti-sun compositions which contain them, alone or combined with lipophilic sunscreen agents, no longer provide the initial protection desired, when the substrate (skin or hair) to which they have been applied comes into contact with water.

In patent application EP A-0275719, an attempt was made to impart substantivity and water-resistance to anti-sun compositions containing acid screening agents, by combining these agents with a fatty amine.

This type of solution is unsatisfactory in certain cases, because of the impossibility of combining certain acidic screening agents with fatty amines and, also, because fatty amines may cause contact allergies, as is described in the work "Adverse reactions to cosmetics" (Anton de Cornelis de Groot—Ed. Rijksuniversiteit Groningen, 1988) chapter 5, p. 170 et seq.

Now, however, the Applicant has discovered a novel screening cosmetic composition of the type employing a hydrophilic screening agent comprising at least one sulphonic acid group, which overcomes the disadvantages of the prior art and which, moreover, is of enhanced substantivity and water-resistance.

The protection index or PI may be expressed by the ratio of the period of irradiation necessary to reach the erythematogenic threshold with the UV screening agent to the period which is necessary to reach the erythematogenic threshold without a UV screening agent.

The enhancement of these properties is particularly advantageous in the case of anti-sun compositions in the form of oil-in-water emulsions.

In the case of oil-in-water or water-in-oil emulsions, the hydrophilic screening agents are present in the aqueous phase and the lipophilic screening agents in the fatty phase. However, oil-in-water emulsions are regarded much more highly by the consumer than water-in-oil emulsions, because of their pleasant feel (similar to water) and their presentation in the form of a non-greasy cream or milk; however, they also lose their effectiveness in UV protection more easily when they come into contact with water, this loss of protection index by removal of the hydrophilic sunscreen agent with water being all the more marked because the lipophilic-hydrophilic screening combination which is present in the composition is synergic with respect to the protection index.

The subject of the present invention is therefore a screening cosmetic composition, characterized in that it comprises, in a cosmetically acceptable vehicle, at least one hydrophilic agent which screens ultraviolet radiation and comprises at least one sulphonic acid radical ($-SO_3H$) and at least one amino-functional silica derivative.

It should be noted here that the present invention is not suitable for compositions which are to contain hydrophilic screening agents containing a carboxyl radical, since the persistence in water of this type of screening agent is not enhanced by carrying out the combination in accordance with the invention.

Examples of acidic filters containing at least one $SO_3H$ group are the sulphonic derivatives of 3-benzylidene-2-bornanone and, in particular, those of the following formulae (I), (II), (III), (IV), and (V):

Formula (I):

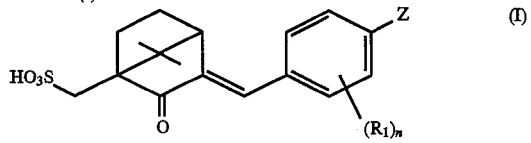

in which:

Z denotes a group

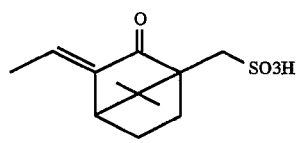

n is equal to 0 or is an integer between 1 and 4 ($0 \leq n \leq 4$)

$R_1$ represents one or more linear or branched alkyl or alkoxy radicals which are identical or different and contain about 1 to 4 carbon atoms.

A particularly preferred compound of formula I is that corresponding to n=0: benzene-1,4-[di(3-methylidenecamphor-10-sulphonic)] acid.

Formula (II):

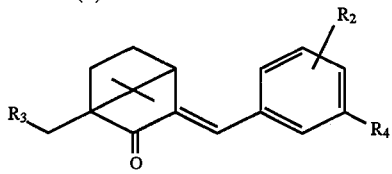

in which:

R$_2$ denotes a hydrogen atom, a halogen atom, an alkyl radical containing about 1 to 4 carbon atoms or a —SO$_3$H radical.

R$_3$ and R$_4$ denote a hydrogen atom or a —SO$_3$H radical, at least one of the radicals R$_2$, R$_3$ or R$_4$ denoting the —SO$_3$H radical, and R$_2$ and R$_4$ being unable simultaneously to denote a —SO$_3$H radical.

Particular examples which may be mentioned are the following compounds of formula II in which:

R$_2$ denotes the —SO$_3$H radical in the para position of benzylidenecamphor and R$_2$ and R$_4$ each denote a hydrogen atom, that is to say 4-(3-methylidenecamphor) benzenesulphonic acid.

R$_2$ and R$_4$ each denote a hydrogen atom and R$_3$ denotes a —SO$_3$H radical, that is to say 3-benzylidenecamphor-10-sulphonic acid.

R$_2$ denotes a methyl radical in the para position of the benzylidenecamphor, R$_4$ denotes a —SO$_3$H radical and R$_3$ denotes a hydrogen atom, that is to say 2-methyl-5-(3-methylidenecamphor)benzenesulphonic acid.

R$_2$ denotes a chlorine atom in the para position of the benzylidenecamphor, R$_4$ denotes a —SO$_3$H radical and R$_3$ denotes a hydrogen atom, that is to say 2-chloro-5-(3-methylidenecamphor) benzenesulphonic acid.

R$_2$ denotes a methyl radical in the para position of the benzylidenecamphor, R$_4$ denotes a hydrogen atom and R$_3$ denotes a —SO$_3$H radical, that is to say 3-(4-methyl) benzylidenecamphor-10-sulphonic acid.

Formula (III):

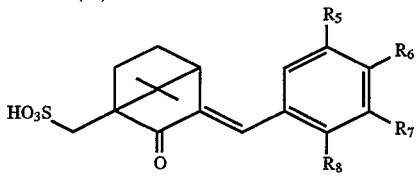

in which:

R$_5$ and R$_7$ denote a hydrogen atom, a hydroxyl radical or a linear or branched, alkyl or alkoxy radical containing about 1 to 8 carbon atoms, at least one of the radicals R$_5$ and R$_7$ representing a hydroxyl, alkyl or alkoxy radical, R$_6$ and R$_8$ denote a hydrogen atom or a hydroxyl radical, at least one of the radicals R$_6$ and R$_8$ denoting the hydroxyl radical, with the proviso that, when R$_5$ and R$_8$ denote a hydrogen atom and R$_6$ denotes a hydroxyl radical, R$_7$ does not denote an alkoxy radical or a hydrogen atom.

Particular examples which may be mentioned are the following compounds of formula (III) in which:

R$_5$ is a methyl radical, R$_6$ is a hydrogen atom, R$_7$ is a tert-butyl radical and R$_8$ is a hydroxyl radical, that is to say (3-t-butyl-2-hydroxy-5-methyl) benzylidenecamphor-10-sulphonic acid.

R$_5$ is a methoxy radical, R$_6$ is a hydrogen atom, R$_7$ is a tert-butyl radical and R$_8$ is a hydroxyl radical, that is to say (3-t-butyl-2-hydroxy-5-methoxy) benzylidenecamphor-10-sulphonic acid.

R$_5$ and R$_7$ each denote a tert-butyl radical, R$_6$ denotes a hydroxyl radical and R$_8$ denotes a hydrogen atom, that is to say (3,5-di-tert-butyl-4-hydroxy) benzylidenecamphor-10-sulphonic acid.

Formula (IV):

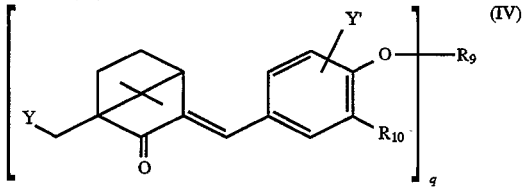

in which:

R$_9$ denotes a hydrogen atom, a linear or branched alkyl radical containing about 1 to 18 carbon atoms, a linear or branched alkenyl radical containing about 3 to 18 carbon atoms, a group $$-CH_2-CHOH\ ,\ -(CH_2CH_2O)_n-H,$$
$$|$$
$$CH_2OH$$

or $-CH_2-CHOH-CH_3$, or else a divalent radical: $-(CH_2)_m-$ or $-CH_2-CHOH-CH_3-$ n being an integer between 1 and 6 ($1 \leq n \leq 6$) and m being an integer between 1 and 10 ($1 \leq m \leq 10$).

R$_{10}$ denotes a hydrogen atom, an alkoxy radical containing about 1 to 4 carbon atoms or a divalent radical —O—, which is linked to the radical R$_9$ when the latter is also divalent, q denotes an integer equal to 1 or 2, it being understood that, if q is equal to 2, R$_9$ must denote a divalent radical, Y and Y' denote a hydrogen atom or a —SO$_3$H radical, and at least one of these radicals Y or Y' is different from hydrogen.

Particular examples which may be mentioned are the following compounds of formula (IV) in which:

q is equal to 1, Y and R$_{10}$ each denote a hydrogen atom, R$_9$ denotes a methyl radical and Y' in position 3 denotes a —SO$_3$H radical, that is to say 2-methoxy-5-(3-methylidenecamphor) benzenesulphonic acid.

q is equal to 1, Y denotes a —SO$_3$H radical, Y' denotes a hydrogen atom and R$_{10}$ denotes a divalent radical —O— which is linked to R$_9$ denoting a methylene radical, that is to say 3-(4,5-methylenedioxy) benzylidenecamphor-10-sulphonic acid.

q is equal to 1, Y denotes a —SO$_3$H radical, both Y' and R$_{10}$ denote a hydrogen atom and R$_9$ denotes a methyl radical, that is say 3-(4-methoxy)benzylidenecamphor-10-sulphonic acid.

q is equal to 1, Y denotes a —SO$_3$H radical, Y' denotes a hydrogen atom; R$_9$ denotes a methyl radical and R$_{10}$ denotes a methoxy radical, that is to say 3-(4,5-dimethoxy) benzylidenecamphor-10-sulphonic acid.

q is equal to 1, Y denotes a SO$_3$H radical, both Y' and R$_{10}$ denote a hydrogen atom; R$_9$ denotes a n-butyl radical, that is to say 3-(4-n-butoxy) benzylidenecamphor-10-sulphonic acid.

q is equal to 1, Y denotes a —SO$_3$H radical, Y' denotes a hydrogen atoms R$_9$ denotes a n-buryl radical and R$_{10}$ denotes a methoxy radical, that is to say 3-(4-n-butoxy-5-methoxy) benzylidenecamphor-10-sulphonic acid.

Formula (V)

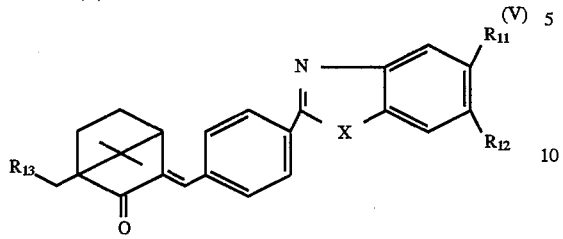

in which:

R$_{11}$ denotes a hydrogen atom, a linear or branched, alkyl or alkoxy radical containing about 1 to 6 carbon atoms or a —SO$_3$H radical, R$_{12}$ denotes a hydrogen atom or a linear or branched, alkyl or alkoxy radical containing about 1 to 6 carbon atoms, R$_{13}$ denotes a hydrogen atom or a —SO$_3$H radical, at least one of the radicals R$_{11}$ and R$_{13}$ denoting a —SO$_3$H radical, X is an oxygen or sulphur atom or a group —NR—, R, being a hydrogen atom or a linear or branched alkyl radical containing about 1 to 6 carbon atoms.

A particular example of formula (V) which may be mentioned is: the compound in which X denotes a —NH— radical, R$_{11}$ denotes a —SO$_3$H radical, and both R$_{12}$ and R$_{13}$ denote a hydrogen atom, that is to say 2-[4-(camphormethylidene) phenyl]benzimidazole-5-sulphonic acid.

The compounds of structures (I), (II), (III), (IV), (V) are described, respectively, in the patent U.S. Pat. No. 4,585,597 and the patents FR 2,236,515, 2,282,426, 2,645,148, 2,430, 938, 2,592,380.

The screening agent containing sulphonic groups may also be a sulphonic derivative of benzophenone, of formula (VI):

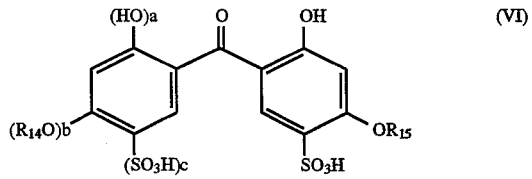

in which:

R$_{14}$ and R$_{15}$, which are identical or different, denote either a hydrogen atom or a linear or branched alkyl radical containing about 1 to 8 carbon atoms.

a, b and c, which are identical or different, are equal to 0 or 1.

A particular example of formula (VI) which may be mentioned is: 2-hydroxy-4-methoxybenzophenone-5-sulphonic acid (compound of formula VI in which a, b and c are equal to zero, and R$_{15}$ denotes a methyl radical).

The screening agent containing sulphonic groups may alternatively be a sulphonic derivative of benzimidazole, of formula:

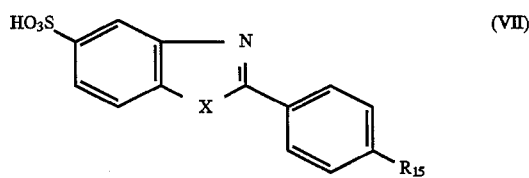

in which:

X denotes an oxygen atom or a —NH— radical

R$_{16}$ denotes a hydrogen atom, a linear or branched, alkyl or alkoxy radical containing about 1 to 8 carbon atoms or a group of formula

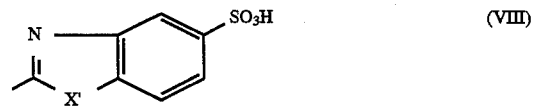

in which X' represents an oxygen atom or a —NH— radical.

Particular examples which may be mentioned are the following compounds of formula (VII) in which:

X denotes the —NH— radical and R$_{16}$ denotes a hydrogen atom: 2-phenylbenzimidazole-5-sulphonic acid.

X denotes the —NH— radical and R$_{16}$ denotes the group of formula (VIII) in which X' denotes the —NH— radical: benzene-1,4-di(benzimidazol-2-yl-5-sulphonic) acid.

X denotes an oxygen atom and R$_{16}$ denotes the group of formula (VIII) in which X' denotes an oxygen atom: benzene-1,4-di(benzoxazol-2-yl-5-sulphonic) acid.

The compounds of formula VI and VII are known compounds which can be prepared according to conventional methods described in the prior art.

The amino-functional silicone derivative which is used in the context of the present invention is useful as a hydrophobic compound which neutralizes the sulphonic acid function of the hydrophilic screening agent, neutralization being obtained with a quantity of silicone derivative which is compatible with the realization of a cosmetic composition.

According to a preferred embodiment of the invention, the amino-functional silicone derivative has an amine index of greater than approximately 0.25 meq/g. Still more preferably this index is greater than approximately 0.50.

In the composition according to the invention the amino-functional silicone derivative may be a silicone derivative comprising at least one primary, secondary or tertiary amine function.

Examples of such compounds which may be mentioned are:

(a) silicones carrying a NH$_2$ radical, such as, for example:
polydimethylsiloxanes (PDMS) α,ω-hydroxylated on the principal chain, which are named in the CTFA dictionary 1991, 4th ed. as AMODIMETHICONE; examples are Silicone Fluid L650 sold by WACKER SILICONE having an amine index of 2.7 to 3.2 meq/gram, Silicone Fluid L655 from WACKER SILICONE having an amine index of 1.3 to 1.45 meq/gram, and Silicone Fluid L656 from WACKER SILICONE having an amine index of 1.2 to 1.4 meq/gram.

polydimethylsiloxanes (PDMS) α,ω-alkylated on the principal chain, for instance the α,ω-trimethylated PDMSs such as those corresponding to the name TRIMETHYLSILYLAMODIMETHICONE in the CTFA dictionary 1991, 4th ed., among which particular mention may be made of X$_2$-8260 sold by the company DOW CORNING with an amine index of 2.8 meq/ grams or SLM 55051/3 sold by the company WACKER having an amine index of 0.47 meq/gram, and the dimethyl-$C_{12}$-alkyl PDMSs such as SLM 23056/1 sold by the company WACKER having an amine index of 1.2 meq/gram.

α,ω-trimethylated polymethylalkyl (fatty) arylalkylsiloxane, such as SLM 23056/2 sold by the company WACKER having an amine index of 1.3 meq/gram.

PDMSs obtained by copolymerization of a difunctional silane and a monomer $CH_3$ —$Si(OR)_2$—$(CH_2)_3$—$NH_2$ in which R is an ethyl and/or methyl radical, such as RHODORSIL Huile PL 1300 sold by the company RHONE POULENC, having an amine index of 0.92 meq/gram.

PDMSs in which the $NH_2$ radical is in the α and ω position on an alkyl site, such as the products TEGO-MER A-SI 2120, with an amine index of 1.95 meq/gram and TEGOMER A-SI 2320 with an amine index of 0.86 meq/gram, both sold by the company GOLD-SCHMIDT.

(b) silicones carrying a —NH— radical, such as the products corresponding to the name AMINOBISPROPY-LDIMETHICONE in the CTFA dictionary 1991, 4th ed., among which there may be mentioned UCARE SILICONE ALE 56 sold by the company UNION CARBIDE, with an amine index of 0.86 meq/gram, (c) the silicones carrying a radical

for instance the compound of structure:

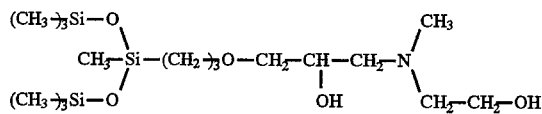

which is a known compound (RN 56039-74-8) with an amine index equal to 2.58 meq/gram.

Examples of preferred screening cosmetic compositions comprise the following combinations of hydrophilic UV screening agent containing one or more sulphonic acid functions and an amino-functional silicone derivative:

sulphonic derivative of 3-benzylidene-2-bornanone of formula (I) in which n=0 (benzene-1,4-(di(3-methylidenecamphor-10-sulphonic)) acid), neutralized to the extent of 100% by a polydimethylsiloxane obtained by copolymerization of a difunctional silane and a monomer $CH_3$—$Si(OR)_2$—$(CH_2)_3$—$NH_2$ in which R is ethyl and/or methyl (Rhodorsil Huile PL 1300 sold by Rhône-Poulenc—amine index 0.92 meq/g).

sulphonic derivative of benzophenone of formula (VI) in which a, b and c are equal to 0, and $R_{15}$ denotes a methyl radical (2-hydroxy-4-methoxybenzophenone-5-sulphonic acid: Uvinul MS 40 sold by BASF), neutralized to the extent of 100% by the abovementioned amino-functional silicone derivative Rhodorsil Huile PL 1300.

sulphonic derivative of benzimidazole of formula (VII) in which X denotes the —NH— radical $R_{16}$ denotes a hydrogen atom (2-phenylbenzimidazole-5-sulphonic acid: Eusolex 232 sold by MERCK), neutralized to the extent of 100% by a polydimethylsiloxane of the AMODIMETHICONE type, sold under the name Silicone Fluid L656 by Wacker Silicone (amine index of 1.2 to 1.4 meq/g).

The hydrophilic UV screening agent comprising at least one sulphonic acid radical is generally present in the screening compositions according to the invention at a total concentration of between approximately 0.2 and 10%, and preferably approximately 0.5 and 5%, relative to the total weight of the composition.

The amino-functional silicone derivative is preferably present in the screening compositions in a proportion which is necessary for the neutralization, to the extent of at least 50%, of the sulphonic acid functions of the hydrophilic screening agent.

Even more preferably, this quantity corresponds to the neutralization of 100% of the sulphonic acid functions.

The cosmetic compositions according to the invention may contain one or more additional hydrophilic or lipophilic sunscreens which are active in UVA and/or UVB which are different, of course, from the acidic hydrophilic screening agents of the invention.

These additional screening agents are preferably chosen from cinnamic derivatives such as, for example, 2-ethylhexyl p-methoxycinnsmate, salicylate derivatives such as, for example, 2-ethylhexyl salicylate and homomenthyl salicylate, camphor derivatives such as, for example, 3-(4-methylbenzylidene) camphor, triazine derivatives such as 2,4,6-tris[p-(2'-ethylhexyl-1'-oxycarbonyl)anilino]-1,3,5-triazine, benzophenone derivatives such as 2-hydroxy-4-methoxybenzophenone, dibenzoylmethane derivatives such as 4-tert-butyl-4'-methoxydibenzoylmethane, β,β-diphenylacrylate derivatives such as 2-ethylhexyl α-cyano-β,β-diphenylacrylate, p-inobenzoic acid derivatives such as, for example, octyl para-dimethylaminobenzoate, menthyl anthranilate, and the polymer screening agents and silicone screening agents described in the application WO-93-04665.

The cosmetic compositions according to the invention may also contain coated or non-coated metal oxide nanopigments such as, for example, titanium oxide, iron oxide, zinc oxide or cerium oxide nanopigments.

Coated or non-coated metal oxide nanopigments are described, in particular, in the application EP 0518,772.

The compositions of the invention may additionally contain cosmetic adjuvants which are chosen from fats, organic solvents, nonionic thickeners, emollients, antioxidants, opacifying agents, stabilizers, silicones other than those already described, anti-foaming agents, moisturizing agents, vitamins, fragrances, preservatives, nonionic surfactants, fillers, sequestering agents, nonionic polymers, propellants, basifying or acidifying agents, dyes or any other ingredient which is commonly used in cosmetics.

The fats may consist of an oil or a wax or a mixture thereof, petroleum jelly, paraffin, lanolin, hydrogenated lanolin, acetylated lanolin; they also comprise fatty acids, fatty alcohols such as lauryl alcohol, cetyl alcohol, myristal alcohol, stearyl alcohol, palmityl alcohol, oleyl alcohol and 2-octyldodecanol, fatty acid esters such as glycerol monostearate, polyethylene glycol monostearate, isopropyl myristate, isopropyl adipate, isopropyl palmitate and octyl palmitate, the benzoates of $C_{12}$–$C_{15}$ fatty alcohols (Finsolv TN from FINETEX), myristyl alcohol polyoxypropylenated with 3 moles of propylene oxide (WITCONOL APM from WITCO), and $C_6$–$C_{18}$ fatty acid triglycerides such as the triglycerides of caprylic/capric acid.

The oils are chosen from animal, vegetable, mineral or synthetic oils and, in particular, hydrogenated palm oil, hydrogenated castor oil, liquid petroleum, paraffin oil, Purcellin oil (stearyl octanoate), silicone oils and isoparaffins.

The waxes are chosen from animal, fossil, vegetable, mineral or synthetic waxes. Those which may be mentioned in particular are beeswaxes, carnauba waxes, candelilla wax, sugar-cane wax, Japan wax, ozocerites, montan wax, microcrystalline waxes, paraffins, and silicone waxes and resins.

The organic solvents which may be mentioned include lower polyols and alcohols such as ethanol, isopropanol, propylene glycol, glycerol and sorbitol.

Thickeners, which are preferably nonionic, may be chosen from guar gums and modified or non-modified celluloses, such as hydroxypropylated guar gum, cetylhydroxyethylcellulose, silicas such as, for example, Bentone Gel MiO sold by the company NL INDUSTRIES or Veegum Ultra sold by the company POLYPLASTIC.

The compositions of the invention are prepared in accordance with techniques which are well known to those skilled in the art. When preparing the composition it is possible to form a paste from the acidic screening agent and the amino-functional silicone derivative and then to add the other constituents of the composition and homogenize them. It is also possible to react them beforehand, for example by addition of a solution of the amino-functional silicone derivative in ethanol or dichloromethane to an aqueous solution of the acidic screening agent, followed by evaporation of the solvent, and to introduce the product of this reaction into the composition.

The cosmetic composition of the invention may be used as a protective composition for the human skin or hair against ultraviolet radiation, as an anti-sun composition or as a make-up product.

This composition may be presented, in particular, in the form of an emulsion such as a cream, a milk or a cream gel, a powder, a solid stick and, optionally, may be packaged as an aerosol and may be presented in the form of a mousse or spray.

When the composition is an emulsion, the aqueous phase of the latter may comprise a nonionic vesicle dispersion prepared according to known processes (Bangham, Standish and Watkins, J. Mol. Biol. 13, 238 (1965), FR 2315991 and FR 2416008.

Another subject of the present invention is a method for cosmetic treatment of the skin or hair which is intended to protect them against the effects of UV radiation and which consists in applying to the skin or hair an effective quantity of a cosmetic composition as defined above.

When the cosmetic composition according to the invention is used for the protection of human skin against UV radiation or as an anti-sun composition, it may be presented in the form of a suspension or dispersion in solvents or fats, in the form of a nonionic vesicle dispersion or else in the form of an emulsion such as a cream or a milk, in the form of an ointment, gel, solid stick, aerosol mousse or spray.

When the cosmetic composition according to the invention is used for the protection of hair, it may be presented in the form of a shampoo, lotion, gel, emulsion, nonionic vesicle dispersion or hair lacquer and may constitute, for example, a rinsing composition to be applied before or after shampooing, before or after dyeing or bleaching, before, during or after a permanent-waving or hair-straightening operation, as a treating or styling lotion or gel, as a lotion or gel for blow drying or setting, or a composition for the permanent waving, straightening, dyeing or bleaching of hair.

When the composition is used as a make-up product for the eyelashes, eyebrows or skin, such as a skin treatment cream, a foundation, a lipstick, an eyeshadow, a blusher, a mascara or a liner, also called eyeliner, it may be presented in a solid or pasty form, in an anhydrous or aqueous form, such as oil-in-water or water-in-oil emulsions, nonionic vesicle dispersions or else suspensions.

One other subject of the invention is a screening combination which comprises, on the one hand, a hydrophilic screening agent containing at least one sulphonic acid radical as described above and, on the other hand, an amino-functional silicone derivative as also described above.

The amino-functional silicone derivative is preferably present in a proportion which is necessary for the neutralization of at least 50% of the sulphonic acid functions of the hydrophilic screening agent.

Even more preferably the amino-functional silicone derivative is present in a proportion which is necessary for the neutralization of 100% of the sulphonic acid functions of the hydrophilic screening agent.

Another subject of the present invention is the use of the above combination for the preparation of cosmetic compositions.

The invention will be illustrated more fully by the examples below, which should not be considered as applying any limitation whatsoever.:

EXAMPLE 1

Anti-sun composition for the skin (oil-in-water emulsion)

| | |
|---|---|
| Mixture (80/20) of cetylstearyl alcohol and cetylstearyl alcohol oxyethylenated with 33 moles of ethylene oxide, sold under the name SINNOWAX AO by the company Henkel | 7 g |
| Glycerol stearate | 2 g |
| Cetyl alcohol | 1.5 g |
| Polydimethylsiloxane: silicone DC200-350 cst from the company Dow Corning | 1.5 g |
| Octyl p-methoxycinnamate | 4 g |
| Octyl 2-cyano-3,3-diphenyl-2-propenoate | 10 g |
| Microtitanium dioxide MT 100T from Tayca | 2 g |
| Silicone Fluid L650 from Wacker Silicone, with an amine index of 2.7 to 3.2 meq/g | 1.18 g |
| Benzene-1,4-[di(3-methylidenecamphor-10-sulphonic)] acid | 1 g |
| Glycerol | 20 g |
| Preservatives qs | |
| Demineralized water qs | 100 g |

The emulsion is produced by adding the fatty phase, heated to around 80° C., to the aqueous phase which contains the preservatives and the glycerine, which has been brought to the same temperature, with rapid stirring.

EXAMPLE 2

Anti-sun composition for the skin: oil-in-water emulsion:

| | |
|---|---|
| Mixture of glycerol stearate and polyethylene glycol stearate containing 100 moles of ethylene oxide, sold under the name ARLACEL 165 by the company ICI | 2 g |
| Glycerol stearate | 2 g |
| Stearyl alcohol | 1 g |
| Octyl 2-cyano-3,3-diphenyl-2-propenoate | 7 g |
| 2-hydroxy-4-methoxybenzophenone-5-sulphonic acid sold under the name UVINUL MS 40 by the company BASF | 2 g |
| Silicone Fluid L655 from WACKER SILICONE, having an amine index of 1.3 to 1.45 meq/g | 5 g |
| Cetylhydroxyethylcellulose (Natrosol Plus Grade 330 CS from AQUALON) | 0.4 g |

-continued

| | |
|---|---|
| Glycerine | 9 g |
| Preservatives qs | |
| Demineralized water qs | 100 g |

This emulsion is produced according to the process described in Example 1, the aqueous phase containing the thickener (cetylhydroxyethylcellulose), the preservatives and the glycerine.

EXAMPLE 3

Anti-sun composition for the skin: oil-in-water emulsion:

| | |
|---|---|
| Mixture of glycerol stearate and polyethylene glycol stearate containing 100 moles of ethylene oxide, sold under the name ARLACEL 165 by the company ICI | 2 g |
| Glycerol stearate | 2 g |
| Stearyl alcohol | 1 g |
| Octyl p-methoxycinnamate | 5 g |
| 2-phenylbenzimidazole-5-sulphonic acid sold under the name EUSOLEX 232 by the company MERCK | 4 g |
| Silicone Fluid L656 from WACKER SILICONE, having an amine index of 1.2 to 1.4 meq/g | 11.23 g |
| Cetylhydroxyethylcellulose (Natrosol Plus Grade 330 CS from AQUALON) | 0.4 g |
| Glycerine | 9 g |
| Preservatives qs | |
| Demineralized water qs | 100 g |

This emulsion is produced according to the process described in Example 2.

EXAMPLE 4

Anti-sun composition for the skin: water-in-oil emulsion:

| | |
|---|---|
| ARLACEL 1689 from ICI (mixture of polyglycerol ricinoleate (3 moles) and Sorbitol oleate) | 3.5 g |
| Liquid petroleum | 10 g |
| Block copolymer of Dodecylglycol/ethylene glycol: Elfacos ST37 from AKZO (stabilizer) | 1 g |
| Polydimethylsiloxane: Silicone DC 200-350 cst from DOW CORNING | 3 g |
| β-hydroxyoctacosanyl 12-hydroxystearate: Elfacos C26 from AKZO (stabilizer) | 5 g |
| Benzene-1,4-[di(3-methylidenecamphor-10-sulphonic)] acid | 2 g |
| Silicone Fluid L650 from WACKER SILICONE having an amine index of 2.7 to 3.2 meq/g | 2.37 g |
| Glycerine | 3 g |
| Preservatives qs | |
| Mixture of dimethiconol (13%) and octamethyl-cyclotetrasiloxane-decamethylcyclopentasiloxane (87%), sold under the name Q2-1401 by the company DOW CORNING | 5 g |
| Demineralized water qs | 100 g |

This emulsion is prepared by adding the aqueous phase containing the preservatives and the glycerine, heated to approximately 80° C., to the fatty phase, which has been brought to the same temperature, with vigorous stirring.

EXAMPLE 5

Anti-sun composition for the skin.

Oil-in-water emulsion in which the aqueous phase contains a nonionic vesicle dispersion.

A nonionic vesicle dispersion is prepared beforehand as follows: a lamellar phase is formed by adding a quantity of hot water (approximately 80° C.) (15.2 g) equivalent to twice the quantity of the following melted lipids:

Nonionic liquid of formula:

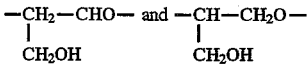 6 g in which:

—$C_3H_5(OH)O$—consists of a mixture of radicals:

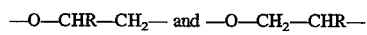

—$O\ C_2H_3(R)$—consists of a mixture of radicals:

—O—CHR—CH$_2$— and —O—CH$_2$—CHR— n is an average statistical value equal to 6

R is a mixture of $C_{14}H_{29}$ and $C_{16}H_{33}$ radicals.

| | |
|---|---|
| Cholesterol | 1.6 g |

After stirring for several minutes using an Ultra-Turrax and returning the mixture to room temperature, a quantity of water at room temperature (22.8 g) which is equivalent to 3 times the quantity of the above lipids and containing 5 g of glycerine is added to said mixture in order to form the vesicle phase, and the mixture is subsequently stirred for several minutes using an Ultra Turrax.

2 g of benzene-1,4-[di(3-methylidenecamphor-10-sulphonic)] acid are then formed into a paste with 7.68 g of Rhodorsil Huile PL 1300 sold by the company Rhône-Poulenc and having an amine index of 0.92 meq/g, to which are added the other components of the fatty phase: 15 g of liquid petroleum and preservatives, and the mixture is brought to 70° C. After returning to room temperature, this fatty phase is then emulsified by the vesicle dispersion prepared above, and then finally the composition is thickened by adding to it 0.2 g of cetylhydroxyethylcellulose (Natrosol Plus Grade 330 CS from Aqualon) and 0.2 g of hydroxypropylated guar gum and preservatives, dissolved in the remaining amount of water required to make the composition up to 100 g.

EXAMPLE 6

Beauty cream for the skin

The procedure of Example 5 is repeated but using 3 g of 1,4[di(3-methylidenecamphor-10-sulphonic)] acid and 5 g of polydimethylsiloxane containing terminal primary amine groups, sold by the company Goldschmidt under the name Tegomer A-SI-2120 with an amine index of 1.95 meq/g, as a replacement for Rhodorsil Huile PL 1300 from Rhône-Poulenc.

EXAMPLE 7

Conditioner

| | |
|---|---|
| 30/70 cetyl/stearyl alcohol ethoxylated 33 EO | 1 g |
| 30/70 cetyl/stearyl alcohol | 4.5 g |
| 2-octyl dodecanol | 0.8 g |
| Glycerine | 0.8 g |
| 50/50 cetyl/stearyl alcohol | 2 g |
| Benzene-1,4-[di(3-methylidenecamphor-10-sulphonic)] acid | 2 g |

13
-continued

| | |
|---|---|
| Silicone Fluid L650 from WACKER silicone having an amine index of 2.7 to 3.2 meq/g | 2.36 g |
| Preservatives qs | |
| Fragrance qs | |
| Purified water qs | 100 g |

This conditioner is prepared in accordance with the process of Example 1.

EXAMPLE 8

Anti-sun composition for the skin: oil-in-water emulsion

| | |
|---|---|
| Mixture of glycerol stearate and polyethylene glycol stearate containing 100 moles of ethylene oxide, sold under the name ARLACEL 165 by the company ICI | 2 g |
| Liquid petroleum | 10 g |
| Glycerol stearate | 2 g |
| Stearyl alcohol | 1 g |
| Glycerine | 9 g |
| Benzene-1,4-(di(3-methylidenecamphor-10-sulphonic)) acid | 3 g |
| Rhodorsil Huile PL 1300 sold by Rhône-Poulenc - amine index 0.92 meq/g | 11.52 g |
| Cetylhydroxyethylcellulose (Natrosol Plus Grade 330 CS from Aqualon) | 0.4 g |
| Preservatives qs | |
| Water qs | 100 g |

This emulsion is prepared in accordance with the process described in Example 2.

EXAMPLE 9

Anti-sun composition for the skin: oil-in-water emulsion

| | |
|---|---|
| Mixture of glycerol stearate and polyethylene glycol stearate containing 100 moles of ethylene oxide, sold under the name ARLACEL 165 by the company ICI | 2 g |
| Liquid petroleum | 10 g |
| Glycerol stearate | 2 g |
| Stearyl alcohol | 1 g |
| Glycerine | 9 g |
| 2-hydroxy-4-methoxybenzophenone-5-sulphonic acid (Uvinul MS 40 from BASF) | 2 g |
| Rhodorsil Huile PL 1300 sold by Rhône-Poulenc - amine index 0.92 meq/g | 7.06 g |
| Cetylhydroxyethylcellulose (Natrosol Plus Grade 330 CS from Aqualon) | 0.4 g |
| Preservatives qs | |
| Water qs | 100 g |

This emulsion is prepared in accordance with the process described in Example 2.

EXAMPLE 10

Anti-sun composition for the skin: oil-in-water emulsion

| | |
|---|---|
| Mixture of glycerol stearate and polyethylene glycol stearate containing 100 moles of ethylene oxide, sold under the name ARLACEL 165 by the company ICI | 2 g |
| Liquid petroleum | 10 g |
| Glycerol stearate | 2 g |
| Stearyl alcohol | 1 g |
| Glycerine | 9 g |

14
-continued

| | |
|---|---|
| 2-Phenyl-benzimidazole-5-sulphonic acid: Eusolex 232 from MERCK | 4 g |
| Silicone Fluid L 656 sold by WACKER SILICONE - amine index 1.2 to 1.4 meq/g | 11.23 g |
| Cetylhydroxyethylcellulose: (Natrosol Plus Grade 330 CS from Aqualon) | 0.4 g |
| Preservatives qs | |
| Water qs | 100 g |

This emulsion is prepared according to the process described in Example 2.

I claim:

1. A cosmetic composition which is adapted to protect the user from ultraviolet radiation which comprises:
   (i) at least one hydrophilic agent which functions to screen ultraviolet radiation comprising at least one sulphonic acid radical —$SO_3H$, and
   (ii) at least one amino-functional silicone derivative,
   and wherein said hydrophilic agent and said silicone derivative are comprised in a cosmetically acceptable vehicle.

2. Composition according to claim 1, wherein the hydrophilic agent which screens ultraviolet radiation is a compound with a 3-benzylidene-2-bornanone structure.

3. Composition according to claim 2, wherein the hydrophilic agent which screens ultraviolet radiation corresponds to the following formula (I):

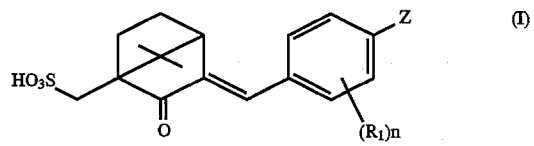

in which:

Z denotes a group of formula:

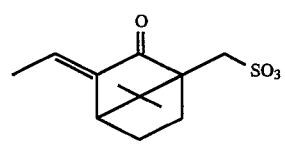

n denotes 0 or an integer greater than or equal to 1 and less than or equal to 4

$R_1$ represents one or more identical or different, linear or branched, alkyl or alkoxy radicals containing 1 to 4 carbon atoms.

4. Composition according to claim 3, wherein the compound of formula (I) is benzene-1,4-[di(3-methylidenecamphor-10-sulphonic)] acid.

5. Composition according to claim 2, wherein the hydrophilic agent which screens ultraviolet radiation corresponds to the following formula (II):

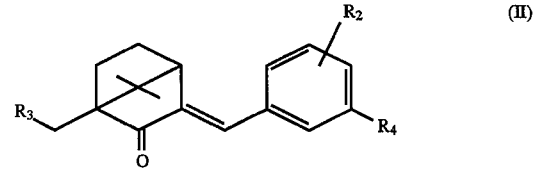

in which $R_2$ denotes a hydrogen atom, a halogen atom, an alkyl radical containing 1 to 4 carbon atoms or a —$SO_3H$ radical $R_3$ and $R_4$ denote a hydrogen atom or a —$SO_3H$ radical, at least one of the radicals $R_2$, $R_3$ or $R_4$ denoting the —$SO_3H$ radical and $R_2$ and $R_4$ being unable simultaneously to denote a —$SO_3H$ radical.

6. Composition according to claim 5, wherein in the formula (II), $R_2$ denotes the —$SO_3H$ radical in the para position of the benzylidenecamphor and $R_3$ and $R_4$ each represent a hydrogen atom.

7. Composition according to claim 5, wherein, in the formula (II), $R_2$ and $R_4$ each represent a hydrogen atom and $R_3$ denotes —$SO_3H$.

8. Composition according to claim 5, wherein, in the formula (II), $R_2$ denotes the methyl radical in the para position of the benzylidenecamphor, $R_4$ denotes a radical represents the radical $SO_3H$ and $R_3$ represents a hydrogen atom.

9. Composition according to claim 5, wherein, in the formula (II) $R_2$ denotes a chlorine atom in the para position of the benzylidenecamphor, $R_4$ denotes the —$SO_3H$ radical and $R_3$ denotes a hydrogen atom.

10. Composition according to claim 5, wherein, in the formula (II), $R_2$ denotes the methyl radical in the para position of the benzylidenecamphor, $R_4$ denotes a hydrogen atom and $R_3$ denotes the —$SO_3H$ radical.

11. Composition according to claim 2, wherein the hydrophilic agent which screens ultraviolet radiation corresponds to the following formula (III):

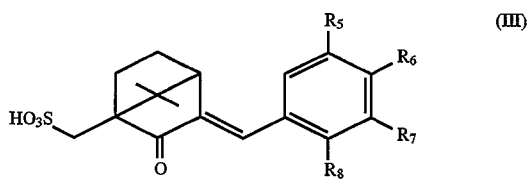

in which:

$R_5$ and $R_7$, which are identical or different, denote a hydrogen atom, a hydroxyl radical, a linear or branched alkyl radical containing 1 to 8 carbon atoms or a linear or branched alkoxy radical containing 1 to 8 carbon atoms, at least one of the radicals $R_5$ and $R_7$ representing a hydroxyl, alkyl or alkoxy radical, $R_6$ and $R_8$, which are identical or different, denote a hydrogen atom or a hydroxyl radical, at least one of the radicals $R_6$ and $R_8$ denote the hydroxyl radical, with the proviso that, when $R_5$ and $R_8$ denote hydrogen and $R_6$ denotes the hydroxyl radical, $R_7$ does not denote an alkoxy radical or a hydrogen atom.

12. Composition according to claim 11, wherein, in the formula (III), $R_5$ is a methyl radical, $R_6$ is a hydrogen atom, $R_7$ is a tert-butyl radical and $R_8$ is a hydroxyl radical.

13. Composition according to claim 11, wherein, in the formula (III), $R_7$ is a methoxy radical, $R_6$ is a hydrogen atom, $R_7$ is a tert-butyl radical and $R_8$ is a hydroxyl radical.

14. Composition according to claim 11, wherein, in the formula (III), $R_5$ and $R_7$ each denote a tert-butyl radical, $R_6$ denotes a hydroxyl radical and $R_8$ denotes a hydrogen atom.

15. Composition according to claim 2, wherein the hydrophilic agent which screens ultraviolet radiation corresponds to the following formula (IV):

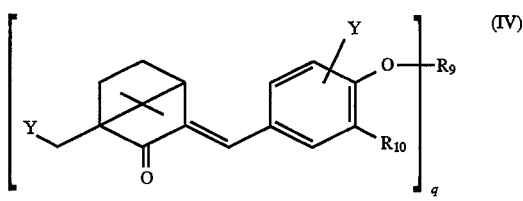

in which $R_9$ denotes a hydrogen atom, a linear or branched alkyl radical containing 1 to 18 carbon atoms, a linear or branched alkenyl radical containing 3 to 18 carbon atoms, a group chosen from the group comprising:

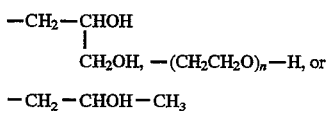

or a divalent radical: —$(CH_2)_m$— or —$CH_2$—$CHOH$—$CH_2$— n being an integer between 1 and 6 ($1 \leq n \leq 6$) and m being an integer between 1 and 10 ($1 \leq m \leq 10$)

$R_{10}$ denotes a hydrogen atom, an alkoxy radical containing 1 to 4 carbon atoms or a divalent radical —O— which is linked to the radical $R_9$ where the latter is also divalent, q denotes an integer equal to 1 or 2, it being understood that, if q is equal to 2, $R_9$ must denote a divalent radical, Y and Y' denote a hydrogen atom or a —$SO_3H$ radical, and at least one of these radicals Y or Y' is different from hydrogen.

16. Composition according to claim 15, wherein, in the formula (IV), q is equal to 1, Y and $R_{10}$ each denote a hydrogen atom, $R_9$ denotes a methyl radical and Y' in position 3 denotes a —$SO_3H$ radical.

17. Composition according to claim 15, wherein, in the formula (IV), q is equal to 1, Y denotes a —$SO_3H$ radical, Y' denotes a hydrogen atom; $R_{10}$ denotes a divalent radical —O— which is linked to $R_9$ denoting a methylene radical.

18. Composition according to claim 15, wherein, in the formula (IV), q is equal to 1, Y denotes a —$SO_3H$ radical, both Y' and $R_{10}$ denote a hydrogen atom; $R_9$ denotes a methyl radical.

19. Composition according to claim 15, wherein, in the formula (IV), q is equal to 1, Y denotes a —$SO_3H$ radical, Y' denotes a hydrogen atom; $R_9$ denotes a methyl radical and $R_{10}$ denotes a methoxy radical.

20. Composition according to claim 15, wherein, in the formula (IV), q is equal to 1, Y denotes a —$SO_3H$ radical, both Y' and $R_{10}$ denote a hydrogen atom; $R_9$ denotes a n-butyl radical.

21. Composition according to claim 15, wherein, in the formula (IV), q is equal to 1, Y denotes a —$SO_3H$ radical, Y' denotes a hydrogen atom; $R_9$ denotes a n-butyl radical and $R_{10}$ denotes a methoxy radical.

22. Composition according to claim 2, characterized in that the hydrophilic agent which screens ultraviolet radiation corresponds to the following formula (V):

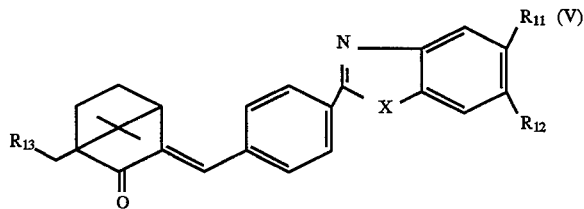

in which:

$R_{11}$ denotes a hydrogen atom, a linear or branched, alkyl or alkoxy radical containing 1 to 6 carbon atoms or a —$SO_3H$ radical, $R_{12}$ denotes a hydrogen atom or a linear or branched, alkyl or alkoxy radical containing 1 to 6 carbon atoms, $R_{13}$ denotes a hydrogen atom or a —$SO_3H$ radical, at least one of the radicals $R_{11}$ to $R_{13}$ denotes a —$SO_3H$ radical.

X is an oxygen or sulphur atom or a group —NR—, R being a hydrogen atom or a linear or branched alkyl radical containing 1 to 6 carbon atoms.

23. Composition according to claim 22, wherein, in the formula (V), X denotes a —NH— radical, $R_n$ denotes a —$SO_3H$ radical, and both $R_{12}$ and $R_{13}$ denote a hydrogen atom.

24. Composition according to claim 1, wherein the hydrophilic agent which screens ultraviolet radiation is a compound of the formula (VI)

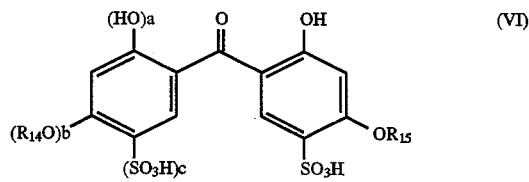

in which $R_{14}$ and $R_{15}$, which are identical or different, denote a hydrogen atom or a linear or branched alkyl radical containing 1 to 8 carbon atoms a, b and c, which are identical or different, are equal to 0 or 1.

25. Composition according to claim 24, wherein, in the formula (VI) a=b=c=0 and $R_{15}$ denotes a methyl radical.

26. Composition according to claim 1, wherein the hydrophilic agent which screens ultraviolet radiation is a compound of the formula (VII)

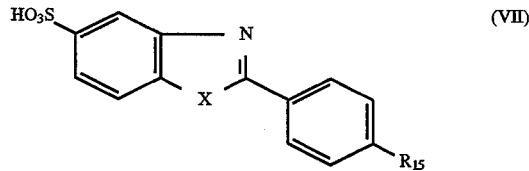

in which

X denotes an oxygen atom or a —NH— radical $R_{16}$ denotes a hydrogen atom, a linear or branched, alkyl or alkoxy radical containing 1 to 8 carbon atoms or a group of formula (VIII)

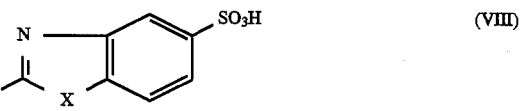

in which X', independently of X, denotes an oxygen atom or a —NH— radical.

27. Composition according to claim 26, wherein, in the formula (VII), X denotes the —N— radical and $R_{16}$ denotes a hydrogen atom.

28. Composition according to claim 26, wherein, in the formula (VII), X denotes the —NH— radical, $R_{16}$ denotes the group of formula (VIII) with X' denoting the —NH— radical.

29. Composition according to claim 26, wherein, in the formula (VII), X denotes an oxygen atom, $R_{14}$ denotes the group of formula (VIII) with X' denoting an oxygen atom.

30. Composition according to claim 1, wherein the amino-functional silicone derivative has an amine index of greater than 0.25 meq/gram.

31. Composition according to claim 30, wherein the amino-functional silicone derivative has an amine index of greater than 0.50 meq/gram.

32. Composition according to claim 1, wherein the amino-functional silicone derivative is a silicone derivative comprising a primary, secondary or tertiary amine function.

33. Composition according to claim 32, wherein the silicone derivative comprises a primary amine function $NH_2$ which is linked to the principal chain via a pendant group, or in the α and ω position on the principal chain.

34. Composition according to claim 32, wherein the silicone derivative comprising a secondary amine function is an aminobispropyldimethicone compound.

35. Composition according to claim 32, wherein the silicone derivative comprising a tertiary amine function is the compound of structure

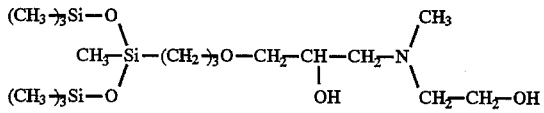

36. Composition according to claim 1, wherein said composition contains from 0.2 to 10% by weight of the hydrophilic agent which screens ultraviolet radiation, and preferably from 0.5 to 5%.

37. Composition according to claim 1, wherein said composition contains the amino-functional silicone derivative in a proportion which is necessary for the neutralization of at least 50% of the sulphonic acid functions of the hydrophilic screening agent.

38. Composition according to claim 1, wherein said composition contains the amino-functional silicone derivative in a proportion which is necessary for the neutralization of 100% of the sulphonic acid functions of the hydrophilic screening agent.

39. Composition according to claim 1, wherein said composition additionally contains one or more additional hydrophilic or lipophilic UVB and/or UVA sunscreens other than acidic hydrophilic screening agents.

40. Composition according to claim 39, wherein the additional sunscreens are chosen from cinnamates, salicylates, benzylidenecamphor derivatives, triazine derivatives, benzophenone derivatives, dibenzoylmethane derivatives, β,β-diphenylacrylate derivatives, p-aminobenzoic acid derivatives, menthyl anthranilate, polymer screening agents and silicone screening agents.

41. Composition according to claim 40, wherein the additional sunscreens are chosen from the group consisting of 4-tert-butyl-4'-methoxydibenzoylmethane, octyl 2-cyano-3,3-diphenyl-2-propenoate and 3-(4-methylbenzylidene) camphor.

42. Composition according to claim 40, wherein the additional sunscreens are chosen from the group consisting of 2-ethylhexyl p-methoxycinnamate, 2,4,6-tris[p-(2'ethylhexyl-1'-oxycarbonyl) anilino]-1,3,5-triazine and octyl 2-cyano-3,3-diphenyl-2-propenoate.

43. Composition according to claim 1, wherein said composition additionally contains coated or non-coated metal oxide nanopigments.

44. Composition according to claim 1, wherein said composition additionally comprises cosmetic adjuvants chosen from fats, organic solvents, nonionic thickeners, emollients, antioxidants, opacifying agents, stabilizers, silicones other than the amino-functional silicone derivatives, anti-foaming agents, moisturizers, fragrances, preservatives, nonionic surfactants, fillers, sequestering agents, nonionic polymers, propellants, basifying or acidifying agents and dyes.

45. Composition according to claim 1, wherein said composition constitutes a protective composition for the human skin or an anti-sun composition and is presented in the form of a nonionic vesicle dispersion, emulsions, cream, milk, gel, cream gel, suspensions, dispersions, powder, solid stick, mousse or spray.

46. Composition according to claim 1, wherein said composition constitutes a make-up composition for the eyelashes, eyebrows or skin and is presented in a solid or paste form, in an anhydrous or aqueous form, as an emulsion, suspension or dispersion.

47. Composition according to claim 1, which is used for the protection of hair against ultraviolet radiation, characterized in that it is presented in the form of a shampoo, lotion, gel, emulsion, nonionic vesicle dispersion or hair lacquer.

48. Composition according to claim 1, wherein said cosmetically acceptable vehicle is an emulsion of the oil-in-water type.

49. Method of cosmetic treatment of the skin and/or hair in order to protect them against the effects of UV radiation with wavelengths of between 280 and 400 nm, said method comprising applying an effective quantity of a substantive screening cosmetic composition as defined in claim 1.

50. Screening combination comprising a hydrophilic screening agent containing at least one sulphonic acid radical according to claim 1, and an amino-functional silicone derivative.

51. Combination according to claim 50, wherein the amino-functional silicone derivative is present in a proportion which is necessary for the neutralization of at least 50% of the sulphonic acid functions of the hydrophilic screening agent.

52. Combination according to claim 50, wherein the amino-functional silicone derivative is present in a proportion which is necessary for the neutralization of 100% of the sulphonic acid functions of the hydrophilic screening agent.

53. Use of the combination according to claim 50 for the preparation of cosmetic compositions.

* * * * *